United States Patent [19]

Hudson et al.

[11] Patent Number: 5,043,662
[45] Date of Patent: Aug. 27, 1991

[54] METHOD AND APPARATUS FOR PRODUCING A UNIFORM MAGNETIC FIELD IN A TEST SAMPLE

[75] Inventors: James E. Hudson; Kenneth B. Lamb, both of Winston-Salem, N.C.

[73] Assignee: Westinghouse Electric Corp., Pittsburgh, Pa.

[21] Appl. No.: 603,039

[22] Filed: Oct. 25, 1990

[51] Int. Cl.$^5$ .................... G01N 27/84; H01F 13/00
[52] U.S. Cl. .................... 324/216; 335/284; 335/286; 324/262
[58] Field of Search .................... 324/213–216, 324/262; 335/284, 285, 286, 287, 296

[56] References Cited

U.S. PATENT DOCUMENTS

| | | | |
|---|---|---|---|
| 2,722,636 | 11/1955 | Minchom | 324/216 X |
| 3,248,876 | 4/1966 | Molina | 324/216 X |
| 3,862,047 | 1/1975 | Weltman et al. | 324/216 X |

*Primary Examiner*—Kenneth A. Wieder
*Assistant Examiner*—Warren S. Edmonds

[57] ABSTRACT

An apparatus for producing a uniform magnetic field in a test sample having an angled end during a magnetic particle test procedure, includes a conductive, angled fixture having a contact surface and an overall shape corresponding to that of the angled end of the test sample, so that when a pulsed current is passed through the blade, the resulting uniform magnetic field permits detection of defect indications in the angled end.

9 Claims, 1 Drawing Sheet

METHOD AND APPARATUS FOR PRODUCING A UNIFORM MAGNETIC FIELD IN A TEST SAMPLE

BACKGROUND OF THE INVENTION

1. Field of the Invention

The present invention relates generally to magnetic particle test procedures and, more specifically, to a fixture used in a magnetic particle test procedure which produces a uniform magnetic field.

2. Description of the Related Art

In the production of crucial components such as steam turbine blades it is very important to detect manufacturing defects which are not visible to the naked eye. Magnetic particle test procedures have been developed whereby a test sample, such as a turbine blade is pulsed with an electric current to generate a magnetic field therein. Then, a solution containing iron oxide particles is sprayed on the test sample and the particles align themselves in the direction of the magnetic field.

Latent cracks produce localized variations in the magnetic field, and these variations are manifest in the distribution of iron-oxide particles from the sprayed-on solution. When the test sample is illluminated with a black light, the variations in the magnetic field attributable to latent cracks are manifest in observable changes in magnetic field.

While magnetic particle test procedures have been used in the past to test for defects in turbine blades, the shape of the blade has been found to effect the ability to achieve a uniform magnetic field in the test sample. The problem of creating a uniform magnetic field is particularly acute for blades of the type known as triple pin blades in which two or more airfoils shrouded together at the top share a common root portion which has an angled end and two or more root "fingers". In particular, it has been found that the magnetic field does not adequately extend into the fingers and over the sloped surfaces of the end of the root portion. This problem can lead to the failure of the magnetic particle test procedures to detect defects in the root portion of the blade.

SUMMARY OF THE INVENTION

An object of the present invention is therefore to provide an apparatus for producing a uniform magnetic field in the test sample as a pulsed current is passed through the test sample, whereby the uniform field permits detection of defect indications on blade areas which would otherwise be missed.

Another object of the present invention is to provide an apparatus for producing a uniform magnetic field in a triple pin rotating blade, whereby the magnetic field imparted in the blade by a pulsed electric current passing uniformly through the blade and in particular between the fingers of the root portion and along the angled sides of the root portion.

Another object of the present invention is to provide a fixture for use in a magnetic particle test procedure which is relatively simple in construction and cost effective to produce.

These and other objects of the invention are met by providing an apparatus for producing a uniform magnetic field in a test sample having an angled end during a magnetic particle test procedure, including a conductive angled fixture having a contact surface and an overall shape corresponding to that of the angled end of the test sample, so that when a pulsed current is passed through the blade, the resulting uniform magnetic field permits detection of defect indications in the angled end.

In another aspect of the present invention, a method of conducting a magnetic particle inspection of a test sample having an angled end includes placing a conductive angled fixture over the angled end of the test sample, clamping the test sample between an axially stationary headstock and an axially movable tailstock, whereby the conductive angled fixture is pressed against and conforms in shape to the angled end of the test sample, pulsing an electric current through the test sample to generate a magnetic field, spraying an iron oxide fluid on the test sample, and illuminating the test sample with a black light to observe defect indications.

These and other features and advantages of the magnetic particle test fixture of the present invention will become more apparent with reference to the following detailed description and drawings.

DETAILED DESCRIPTION OF THE PREFERRED EMBODIMENT

Figure 1:
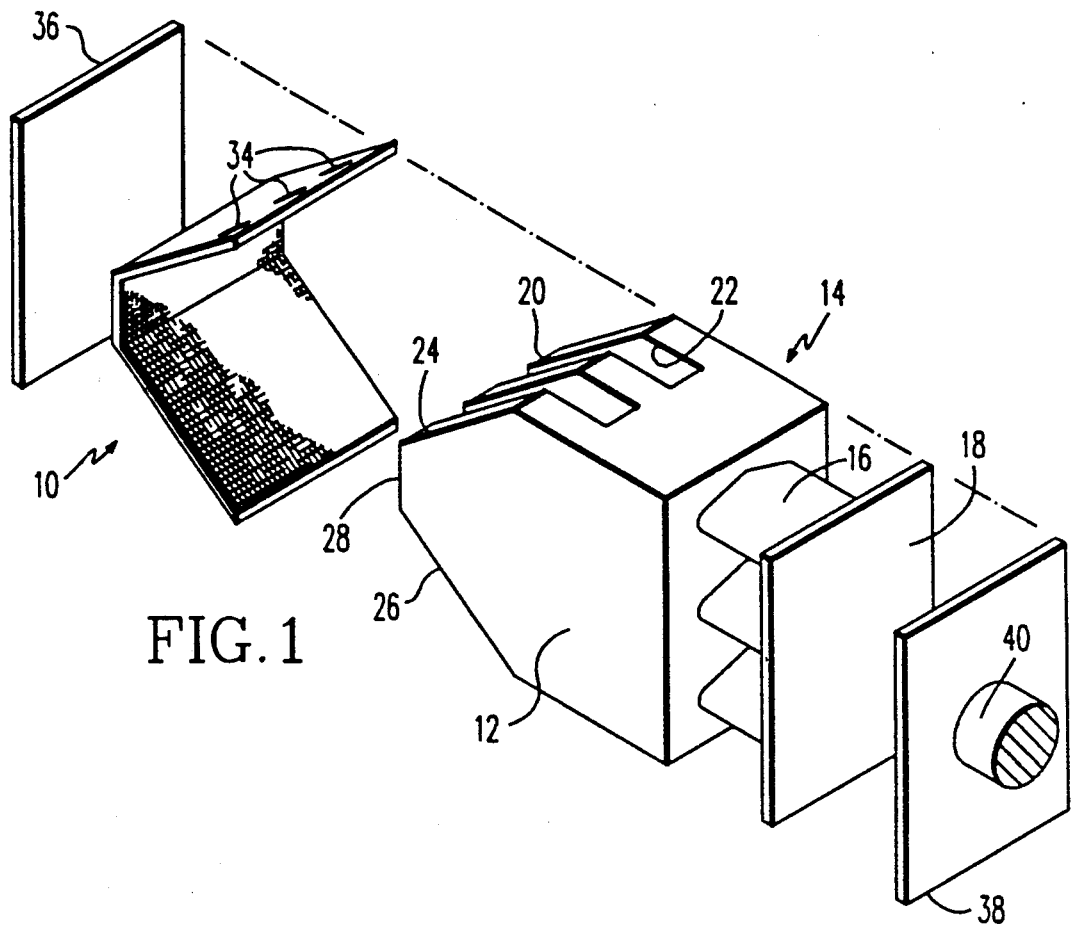
FIG. 1 is a perspective view of a preferred embodiment of the present invention, and showing a triple pin blade and clamping structure.
Figure 2:
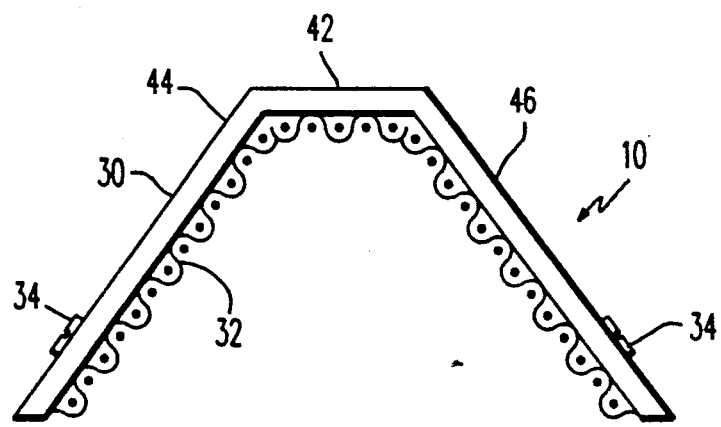
FIG. 2 is a side elevational view showing the magnetic particle test fixture according to the present invention.

Referring now to FIGS. 1 and 2, a fixture 10 is used to produce a uniform magnetic field in a test sample, such as a triple pin blade 12 which has a root portion 14, an airfoil portion 16 and a shroud portion 18. The root portion 14 has tow or more fingers 20 which are spaced apart by one or two axial grooves 22. Opposite sides 24 and 26 of the fingers 20 converge at an angle and terminate at a flat end 28. The airfoil portion !6 is formed from a single stock by electric discharge machining (EDM), while the root portion 14 and the airfoil portion 16 are formed by machining.

After manufacturing by EDM, the present invention is used to check the blade 12 for latent defects. While magnetic particle inspection techniques have been used in the past for other types of turbine blades, the structure of the blade presented in FIG. 1 creates a problem in that the magnetic field imparted in the blade 12 during testing is frequently unevenly distributed, especially around the areas of the converging sides 24 and 26 and in the grooves 22 of the angled end of the test sample (the test sample being a blade structure in FIG. 1 for example).

According to the present invention, a fixture 10 is provided with a three part construction. A backing plate 30 is interconnected with a braided pad 32, with the braided pad 32 being held on an inner surface of the backing plate 30 by bolts 34. Preferably, the backing plate and the braided pad are made of copper, which is electrically conductive. Prior to undertaking the magnetic particle test procedure, the fixture 10 is placed over the angled end of the blade 12, as depicted in FIG. 1. Then, the blade 12 is axially clamped between an axially movable headstock 36 and an axially movable stationary 38. The headstock 38 is driven axially by a hydraulic ram 40 so that the tailstock 38 abuts the shroud portion 18 of the blade 12. At the opposite end, the flat end 28 of the root portion 14 abuts a flat portion 42 of the fixture 10. At the same time, arm portions 44 and 46 of the fixture 10, which are angled at the same angle of convergence of the sides 24 and 26 of the fingers 20 so that the arm portions 44 and 46 contact the sides of the fingers 20. Thus, the headstock and tailstock are brought together so that the fixture 10 is clamped therebetween and over the angled end portion of the blade 12. Then, a pulsed electric current is applied to the blade 12 so as to impart a magnetic field therein. Application of the pulse electric current can be effected by using any of the various known techniques. Then, an iron-oxide particle fluid is sprayed on the blade 12 in the usual manner, using commercially available iron-oxide powder properly mixed. The fluid contains iron-oxide particles which are disbursed in the fluid. When the fluid is sprayed on the magnetized blade 12, the particles will align themselves according to the field lines of the generated magnetic field. Defects in the blade will cause variations in the magnetic field and thus the particles will align themselves accordingly. The alignment of the particles can be visualized by illuminating the blade with a black light. The aforementioned application of an iron-oxide fluid and the use of a black light are known techniques. However, it has been found that the magnetic field is not uniform in the area of the fingers, and generally, the angled end of the blade 12;

The fixture 10 corrects the tendency for the magnetic field to be unevenly disbursed. The copper braided angled plate or fixture 10 is placed on the root end of the triple pin blade 12 and when an electric current is pulsed through the clamp assembly the pulsed current follows the braided pad - blade contact surface. This current flow will generate a circular magnetic field throughout the finger contact area. This magnetic field will provide the means to detect axial directed indications of a defect on all parts of the blade, especially between and on surfaces of the fingers. Normal clamping of only the end of the root fingers does no provide the field on all parts as would be required to obtain an adequate test.

The length of the arm portions 44 and 46 of the fixture 10, as well as the angle of the arms relative to the flat portion 42 can be varied to fit blades having a variety of root finger shapes and sizes. It is understood that the fingers 20 of the blade 12 are used to mount the triple pin blade to a rotor by means of bolts which pass transversely through the end portions of the fingers 20.

Numerous modifications and adaptations of the present invention will be apparent to those so skilled in the art and thus, it is intended by the following claims to cover all such modifications and adaptations which fall within the true spirit and scope of the invention.

What is claimed is:

1. An apparatus for producing a uniform magnetic field in a test sample having a first end and a second angled end during a magnetic particle test procedure, comprising:
    a conductive, angled fixture having an overall shape corresponding to that of the angled end of the test sample, and being fitted on the angled end of the test sample so that when a pulsed current is passed through the test sample from the first end to the second end, a magnetic field is generated uniformly throughout the test sample to ensure detection of defect indications in the angled end.

2. An apparatus as recited in claim 1, wherein the conductive angled fixture includes a backing plate having an inner surface and a wire mesh pad connected to the inner surface of the backing plate, the wire mesh pad being in surface contact with the angled end of the test sample when the pulsed current is passed through.

3. An apparatus as recited in claim 2, wherein the backing plate has two diverging angled segments which fit over the angled end of the test sample.

4. An apparatus as recited in claim 2, wherein the backing plate and the wire mesh pad are made of copper.

5. An apparatus for producing a uniform magnetic field in a triple pin blade having a first end and a second end, the second end defining a root portion with two converging sides and a plurality of fingers, comprising:
    a conductive, angled fixture having an overall shape corresponding to that of the angled end of the triple pin blade, and being fitted on the second end of the blade so that when a pulsed current is passed through the blade from the first end to the second end, a magnetic field is generated uniformly throughout the blade to ensure detection of defect indications on the two converging sides and between the fingers.

6. An apparatus as recited in claim 5, wherein the conductive angled fixture includes a backing plate having an inner surface and a wire mesh pad connected to the inner surface of the backing plate, the wire mesh pad being in surface contact with the root portion of the blade when the pulsed current is passed through.

7. An apparatus as recited in claim 6, wherein the backing plate has two diverging angled segments which fit over the second end of the blade.

8. An apparatus as recited in claim 6, wherein the backing plate and the wire mesh pad are made of copper.

9. A method of producing a uniform magnetic field in a test sample during a magnetic particle inspection of the test sample having an angled and comprising:
    placing a conductive angled fixture on an angled end of the test sample;
    clamping the angled end and an opposite end of the test sample between an axially movable headstock and an axially stationary tailstock, whereby the conductive angled fixture is pressed against and conforms in shape to the angled end of the test sample;
    pulsing an electric current through the test sample to generate a magnetic field;
    spraying an iron-oxide particle fluid on the test sample; and
    illuminating the test sample with a black light to observe defect indications.

* * * * *